United States Patent [19]
Mainzer et al.

[11] Patent Number: 5,677,163
[45] Date of Patent: Oct. 14, 1997

[54] CLEANING COMPOSITIONS COMPRISING THE SUBTILISIN ENZYME ENCODED BY THE GENE SPRC

[75] Inventors: Stanley E. Mainzer, Burlingame; Pushkaraj L. Lad, San Mateo; Brian F. Schmidt, Half Moon Bay, all of Calif.

[73] Assignee: Genencor International, Inc., Rochester, N.Y.

[21] Appl. No.: 431,387

[22] Filed: Apr. 28, 1995

Related U.S. Application Data

[63] Continuation of Ser. No. 950,856, Sep. 24, 1992, abandoned.

[51] Int. Cl.$^6$ .................... C11D 7/42; C11D 9/40; C07K 14/32; C02N 9/54
[52] U.S. Cl. .................... 435/221; 435/69.1; 435/71.2; 435/172.3; 435/252.31; 435/209; 435/210; 435/219; 536/23.2; 536/23.7; 252/174.12
[58] Field of Search .................... 435/221, 69.1, 435/71.2, 172.3, 252.31, 209, 210, 219; 252/174.12; 536/23.2, 23.7

[56] References Cited

U.S. PATENT DOCUMENTS

| | | | |
|---|---|---|---|
| 4,480,037 | 10/1984 | Ichishima et al. | 435/221 |
| 4,764,470 | 8/1988 | Durham et al. | 435/221 |
| 4,771,003 | 9/1988 | Stellwag et al. | 435/221 |
| 4,797,362 | 1/1989 | Takeuchi et al. | 435/221 |

FOREIGN PATENT DOCUMENTS

| | | |
|---|---|---|
| 0 496 361 A2 | 7/1992 | European Pat. Off. |
| WO 88/01293 | 2/1988 | WIPO |
| WO 92/07067 | 4/1992 | WIPO |
| WO 92/17579 | 10/1992 | WIPO |

OTHER PUBLICATIONS

Woodhouse, et al., "Novel Alkaline Protease from Bacillus Isolated from Soil Samples," SIM Abstract, 1989 Annual Meeting.

Schmidt, et al., "Alkalophilic Bacillus sp. Strain LG12 has a Series of Serine Protease Genes," 6th International Conference on Bacilli, Jul. 1991.

*Primary Examiner*—Vasu S. Jagannathan
*Assistant Examiner*—Elizabeth C. Kemmerer
*Attorney, Agent, or Firm*—Kirsten A. Anderson

[57] ABSTRACT

There are described, cleaning compositions comprising proteolytic enzymes having enhanced thermal and/or alkaline stability. Particularly, the compositions comprise a *Bacillus sp.* subtilisin having enhanced thermal stability and alkaline stability. The composition may be useful for any cleaning application such as laundry cleaning, household cleaning (dishcare, hard surface cleaning) or industrial cleaning.

11 Claims, 6 Drawing Sheets

```
              1                                                        50
Lichen   AQTVPYGIPL IKADKVQAQG FKGANVKVAV LDTGIQASHP DLNVVGGASF
Spr-C    AQTVPWGIPH IKADKAHAAG VTGSGVKVAI LDTGIDANHA DLNVKGGASF
Amylo    AQSVPYGVSQ IKAPALHSQG YTGSNVKVAV IDSGIDSSHP DLKVAGGASM
B1147    .QTVVWGISF INTQQAHNRG IFGNGARVAV LDTGI.ATHP DLRIAGGASF
Lentus   AQSVPWGISR VQAPAAHNRG LTGSGVKVAV LDTGI.STHP DLNIRGGASF 51                                                      100
Lichen   VAGEAYN.TD GNGHGTHVAG TVAALDNTTG VLGVAPSVSL YAVKVLNSSG
Spr-C    VSGEPNALQD GNGHGTHVAG TVAALNNTTG VLGVAYNADL YAVKVLSASG
Amylo    VPSETNPFQD NNSHGTHVAG TVAALNNSIG VLGVAPSASL YAVKVLGADG
B1147    ISSEP.SYHD NNGHGTHVAG TIAALNNSIG VLGVAPSADL YAVKVLDRNG
Lentus   VPGEP.STQD GNGHGTHVAG TIAALNNSIG VLGVAPSAEL YAVKVLGASG 101                                                     150
Lichen   SGTYSGIVSG IEWATTNGMD VINMSLGGPS GSTAMKQAVD NAYARGVVVV
Spr-C    SGTLSGIAQG IEWSISNGMN VINMSLGGSS GSTALQQACN NAYNRGIVVI
Amylo    SGQYSWIING IEWAIANNMD VINMSLGGPS GSAALKAAVD KAVASGVVVV
B1147    SGSLASVAQG IEWAINNNMH IINMSLGSTS GSSTLELAVN RANNAGILLV
Lentus   SGSVSSIAQG LEWAGNNGMH VANLSLGSPS PSATLEQAVN SATSRGVLVV 151                                                     200
Lichen   AAAGNSGSSG NTNTIGYPAK YDSVIAVGAV DSNSNRASFS SVGAELEVMA
Spr-C    AAAGNSGSSG NRNTMGYPAR YSSVIAVGAV SSNNTRASFS SVGSELEVMA
Amylo    AAAGNEGTSG SSSTVGYPGK YPSVIAVGAV DSSNQRASFS SVGPELDVMA
B1147    GAAGNTGRQG ....VNYPAR YSGVMAVAAV DQNGQPPSFS TYGPEIEISA
Lentus   AASGNSGAGS ....ISYPAR YANAMAVGAT DQNNNRASFS QYGAGLDIVA 201                                                     250
Lichen   PGAGVYSTYP TSTYATLNGT SMASPHVAGA AALILSKHPN LSASQVRNRL
Spr-C    PGVNILSTTP GNNYASFNGT SMAAPHVAGA AALIKAKYPS MTNVQIRERL
Amylo    PGVSIQSTLP GNKYGAYNGT SMASPHVAGA AALILSKHPN WTNTQVRSSL
B1147    PGVNVNSTYT GNRYVSLSGT SMATPHVAGV AALVKSRYPS YTNNQIRQRI
Lentus   PGVNVQSTYP GSTYASLNGT SMATPHVAGA AALVKQKNPS WSNVQIRNHL 251            275
Lichen   SSTATYLGSS FYYGKGLINV EAAAQ       B. licheniformis    Seq. ID No. 2
Spr-C    KNTATNLGDP FFYGKGVINV ESALQ       LG-12               Seq. ID No. 1
Amylo    ENTTTKLGDS FYYGKGLINV QAAAQ       B. amyloliquefaciens Seq. ID No. 3
B1147    NQTATYLGSP SLYGNGLVHA GRATQ       B. lentus (Esperase) Seq. ID No. 4
Lentus   KNTATSLGST NLYGSGLVNA EAATR       B. lentus (Savinase) Seq. ID No. 5
```

FIGURE 1

```
*  :-> Exact matches (all seqs.);      .  :-> Conservative matches 10        20        30        40        50        60
Amylo   : AQSVPYGVSQIKAPALHSQGYTGSNVKVAVIDSGIDSSHPDLKVAGGASMVPSETNPFQD
PB92    : AQSVPWGISRVQAPAAHNRGLTGSGVRVAVLDTGIST-HPDLNIRGGASFVPGEPST-QD
LG12    : AQTVPWGIPHIKADKAHAAGVTGSGVKVAILDTGIDANHADLNVKGGASFVSGEPNALQD
LGX     : AQTVPYGVPHIKADVAHAQNVTGSGVKVAVLDTGIDASHEDLRVVGGASFVSEEPDALTD
          ** ** *.  . *     *    *** *.**..* **   * **  **** * *       *

70        80        90       100       110       120
Amylo   : NNSHGTHVAGTVAALNNSIGVLGVAPSASLYAVKVLGADGSGQYSWIINGIEWAIANNMD
PB92    : GNGHGTHVAGTIAALNNSIGVLGVAPNAELYAVKVLGASGSGSVSWIAQGLEWAGNNGMH
LG12    : GNGHGTHVAGTVAALNNTTGVLGVAYNADLYAVKVLSASGSGTLSGIAQGIEWSISNGMN
LGX     : GNGHGTHVAGTIAALNNNVGVLGVSYDVDLYAVKVLSAGGSGTLAGIAQGIEWAIDNNMD
           * ********.***** *****      *******  ***    *  *.**     *  *

130       140       150       160       170
Amylo   : VINMSLGGPSGSAALKAAVDKAVASGVVVVAAAGNEGTS-GSSSTVGYPGKYPSVIAVGA
PB92    : VANLSLGSPSPSATLEQAVNSATSRGVLVVAASGNSGAGSIS-----YPARYANAMAVGA
LG12    : VINMSLGGSSGSTALQQACNNAYNRGIVVIAAAGNSGSS-GNRNTMGYPARYSSVIAVGA
LGX     : VINMSLGGSTGSTTLKQASDNAYNSGIVVIAAAGNSGSVLGLVNTIGYPARYDSVIAVGA
          * *.***     *    *  *   *..*.** ** *          **  .*   .****

180       190       200       210       220       230
Amylo   : VDSSNQRASFSSVGPELDVMAPGVSIQSTLPGNKYGAYNGTSMASPHVAGAAALILSKHP
PB92    : TDQNNNRASFSQYGAGLDIVAPGVNVQSTYPGSTYASLNGTSMATPHVAGAAALVKQKNP
LG12    : VSSNNTRASFSSVGSELEVMAPGVNILSTTPGNNYASFNGTSMAAPHVAGAAALIKAKYP
LGX     : VDSNNNRASFSSVGSQLEVMAPGVAINSTLPGNQYGELNGTSMASPHVAGAAALLLAQNP
           * ***** * *...**** . ** **   ****** ********.  *

240       250       260       270
Amylo   : NWTNTQVRSSLENTTTKLGDSFYYGKGLINVQAAAQ      B. amyloliquefaciens Seq.ID No. 3
PB92    : SWSNVQIRNHLKNTATSLGSTNLYGSGLVNAEAATR      B. alcalophilus        Seq.ID No. 6
LG12    : SMTNVQIRERLKNTATNLGDPFFYGKGVINVESALQ                             Seq.ID No. 1
LGX     : NLTNVQRERLRDTATNLGSAFNYGHGVINLERALQ                              Seq.ID No. 7
          *  *.*  * .*  * **   **  *...* . *

CLEANING COMPOSITIONS COMPRISING THE SUBTILISIN ENZYME ENCODED BY THE GENE SPRC

This is a continuation of application Ser. No. 07/950,856 filed Sep. 24, 1992, now abandoned.

the following amino acid sequence:

```
1                                                    50
AQTVPWGIPH  IKADKAHAAG  VTGSGVKVAI  LDTGIDANHA  DLNVKGGASF  VSGEPNALQD  GNGHGTHVAG

100
TVAALNNTTG  VLGVAYNADL  YAVKVLSASG  SGTLSGIAQG  IEWSISNGMN  VINMSLGGSS  GSTALQQACN 150                                                 200
NAYNRGIVVI  AAAGNSGSSG  NRNTMGYPAR  YSSVIAVGAV  SSNNTRASFS  SVGSELEVMA  PGVNILSTTP 250                              275
GNNYASFNGT  SMAAPHVAGA  AALIKAKYPS  MTNVQIRERL  KNTATNLGDP  FFYGKGVINV  ESALQ
```

(Seq. ID No.1); and a suitable cleaning formulation.

FIELD OF THE INVENTION

This invention relates to cleaning compositions comprising a proteolytic enzyme having enhanced alkaline and/or thermal stability. Particularly the compositions comprise a substantially pure subtilisin isolated from *Bacillus sp.* or a variant Bacillus organism, which subtilisin has enhanced alkaline and thermal stability.

BACKGROUND OF THE INVENTION

A wide variety of enzymes, and particularly subtilisins, are well known for use in cleaning compositions such as detergents, dishcare formulations, detergent additives, hard surface cleaners and the like, for laundry cleaning, household and industrial cleaning.

A number of Bacillus subtilisin enzymes are commercially available for use in cleaning compositions, for example, *B. amyloliquefaciens* commercially available from Novo Industries, *B. lentus* (i.e., Savinase™ and Esperase™) commercially available from Novo Industries, and *B. alcalophilus* (Maxacal™) commercially available from Gist-brocades. Because of the diverse nature of cleaning applications there is an ever present need to develop new enzymes which have advantageous properties in different cleaning environments. For example, a dishcare formulation will require a high temperature stable enzyme because of the increased temperatures necessary for use in automatic dishwashers. On the other hand, a laundry detergent composition may be used in cold or hot water, in the presence or absence of bleach, thus, different enzyme activity profiles and stability profiles maybe necessary.

It is the object of the present invention to provide cleaning compositions comprising a novel proteolytic enzyme or mutants or variants thereof, which enzyme has unique kinetic parameters and which has enhanced activity at high temperatures and/or at high pH.

SUMMARY OF THE INVENTION

This invention relates to cleaning compositions comprising a cleaning effective amount of a substantially pure proteolytic enzyme having enhanced thermal stability and an appropriate cleaning formulation. The cleaning compositions of the present invention may be liquid or solid (granular) and may be used for laundry cleaning, household cleaning (i.e., cleaning hard surfaces, dishcare and the like) or industrial cleaning.

Preferably the compositions comprise a substantially pure, thermally stable proteolytic enzyme characterized by In an embodiment of the present invention, the enzyme useful in the cleaning composition is from a variant production strain, preferably a Bacillus strain. Specifically, such embodiment comprises using an enzyme wherein the gene coding for the enzyme LG-12, (sprC) is cloned and expressed in a Bacillus organism, preferably *Bacillus subtilis*. In yet another embodiment of the present invention, the enzyme useful in the cleaning compositions is a mutant or variant enzyme as defined herein and/or the strain producing such enzyme is a mutant or variant strain, as defined herein.

BRIEF DESCRIPTION OF THE DRAWINGS

FIG. 1 shows the amino acid sequence of subtilisins from *B. licheniformis* (SEQ ID NO:2), *B. sp.* (LG-12) (SEQ ID NO:1), *B. amyloliquefaciens* (SEQ ID NO:3), *B. lentus* (Esperase™) (SEQ ID NO:4) and *B. lentus* (Savinase™) (SEQ ID NO:5).

FIG. 2 shows the homology between the amino acid sequences of subtilisins from *B. amyloliquefaciens* (SEQ ID NO:3), *B. alcalophilus* (SEQ ID NO:6), *B. sp.* (LG-12) (SEQ ID NO:1) and *B. sp.* (LGX) (SEQ ID NO:7).

DETAILED DESCRIPTION OF THE INVENTION

Applicants have discovered that novel subtilisin enzymes isolated from *B. sp.* strain, designated LG-12, and particularly the subtilisin enzyme from the gene sprC, designated in FIG. 1 as LG-12, have enhanced thermal stability and, therefore, are useful in cleaning compositions. These compositions may take on a variety of forms such as for laundry cleaning, household and industrial cleaning, and the like. The cleaning compositions comprise suitable cleaning formulations as defined herein, and a proteolytic enzyme (subtilisin) having enhanced thermal stability which can be used to clean a wide variety of materials. The compositions can be added to aqueous solution or solid powder and used according to conventional cleaning techniques.

Enzyme

A preferred enzyme useful in the present invention is a *Bacillus sp.* subtilisin characterized by the amino acid sequence designated as LG-12 in FIG. 1. Unexpectedly, the isolated and purified enzyme is similar in sequence (degree of homology) and synthetic substrate hydrolysis to *B. amy-*

*loliquefaciens* subtilisins, yet has thermal and pH stability profiles similar to *B. lentus* subtilisins, and particularly Esperase™, commercially available from Novo Industries.

Several protease producing strains were isolated from soil known to have neutral to alkaline conditions and then purified. One of the purified protease strains isolated from the soil samples, designated herein as LG-12, produced an enzyme which showed interesting and unique kinetic properties which prompted further study of the enzyme.

It should be understood that the microorganism of the present invention is not limited to the Bacillus strain (LG-12) as natural and artificial mutants or variants of the microorganism can be used. Further, genetic engineering techniques applicable to subtilisin production, such as transformation of corresponding genes (for example, sprC) of the present strain (LG-12) to other host cells, may also be applied and the subtilisin produced by these techniques and then isolated, are included in the present invention. These strains are referred to herein as variant strains.

A mutant or variant strain of LG-12 may be obtained by environmental selection pressure techniques, by UV irradiation, or by the use of mutagenic chemicals as known to those skilled in the art.

A mutant or variant strain may also be produced by genetic manipulation techniques, for example by the transfer of plasmid DNA to a multicopy host or by the excision of the chromosomal genes coding for the protease from the cells of a protease producing bacteria, followed by the cloning of said genes into a suitable vector molecule. Modified enzymes of the present invention encompass such mutant, variant or cloned strains with retained, altered or enhanced ability to produce protease.

It is contemplated in the present invention that the LG-12 protease may be mutated by the introduction of a mutation into isolated DNA encoding the protease, which, upon expression of the DNA, results in the substitution, deletion or insertion of at least one amino acid at a predetermined site in the protease. This method is useful in creating mutants of wild-type proteins (where the "precursor" protein is the wild-type) or reverting mutants to the wild-type (where the "precursor" is the mutant). Such methods are known to those skilled to the art and are described fully in U.S. Pat. No. 4,760,025 now RE 34,606 (issued May 10, 1994) (Estell, et al.) and WO 91/06637 corresponding to U.S. Pat. No. 5,185,258, which are incorporated herein by reference.

For production, a subtilisin producing microorganism belonging to the genus Bacillus may be cultured in a medium for enzyme isolation and purification, as described herein and as known to those skilled in the art. Liquid or solid culture can be used. Culturing conditions and temperatures may vary depending on the desired rate of growth of the microorganism and such methods are known to those skilled in the art.

Isolation of LG-12 Strain

A soil sample was collected from the Los Gatos Creek in Northern California, which runs at high pH's in the winter months. The sample was incubated at 55° C. for two and a half hours to select for the spore formers. It was then inoculated into five different enrichment media which included: gravy; starch carbonate broths, one with raw soy meal and one without; a carbonate only media and a media with raw soy meal. All of the enrichment media were at pH 10, and were made with tap water. The cultures were then plated onto media at pH 7.5 and pH 10.

It was seen that the most preferred pH was 10, as expected. After close inspection, 17 different colony morphologies were found; of these 15 were found to be protease producers as determined by a 1% skim milk assay, such as described in commonly owned U.S. Pat. No. 4,760,025 now RE 34,606 (issued May 10, 1994) which is incorporated herein by reference.

The protease producers were then grown up to 100 ml and concentrated using ammonium sulphate precipitations. (Dixon, M. and Webb, E. C. (1979) Enzymes, pp. 31–33). The purified isolates were then assayed for their activities on synthetic substrates, sAAPFpNA and sAAApNA, by methods as described in Estell, et al., J. Biol. Chem 260:6518, 1985. From the activity screen, LG-12 was selected for further study.

Using SDS-PAGE, the LG-12 protease was estimated to be a protein of approximately 27,000–29,000 molecular weight. When examined by immunoblot analysis, antisera against proteases from *B. amyloliquefaciens, B. licheniformis* and *B. subtilis* exhibited some cross-reactivity with LG-12 protease. However, antisera against *B. lentus* protease, (Savinase™ and Maxacal™) showed no cross-reactivity.

The ability of LG-12 protease to hydrolyze various commercial synthetic substrates was tested as compared to other proteases from different Bacillus organisms, as described herein. From such comparative testing it was determined that LG-12 protease has a substrate profile more similar to *B. amyloliquefaciens* protease than *B. lentus* protease. As described below, this substrate profile is significant in terms of distinguishing this novel enzyme from previously described Bacillus enzymes, since LG-12 protease has an alkaline and thermal stability profile similar to *B. lentus* proteases but a substrate profile similar to *B. amyloliquefaciens*. Biochemical characterization of LG-12 protease indicated its value for the industrial applications.

Cloning of LG-12 Protease Gene

The alkalophilic *Bacillus sp.*, designated as LG-12, was isolated as described above and found to produce at least two extracellular proteases. Using the *B. amyloliquefaciens* subtilisin gene as a probe, the 3' portion of a protease gene (sprD) from *Bacillus sp.* strain LG-12 was cloned on a 0.9 kilobase pair (kb) HindIII fragment, shown in FIG. 3. Three additional serine protease genes (sprA, sprB, and sprC) were discovered on an approximately 6 kb BglII fragment just upstream of the sprD gene. When partial amino acid sequence of the pure enzyme was compared to the amino acid sequence of the cloned genes, LG-12 protease was identified as the product of the sprC gene. The product of sprD is referred to as LGX.

Based on the nucleotide sequence, the mature sprC (LG-12) and sprD (LGX) proteases are 77% identical to each other and about 65% identical to the *B. amyloliquefaciens* subtilisin. Although LG-12 and LGX are substantially homologous from a sequence perspective, these enzymes have different biochemical properties. One of the differences is that in a standard purification protocol, at pH 6.2 LGX binds to DEAE-Trisacryl, but LG-12 does not. LGX bound to DEAE-Trisacryl is eluted with 0.2–0.4M NaCl. This suggests that compared to LG-12, LGX has a greater number of net negative charges on the surface (at pH 6.2). When characterized immunochemically, LGX showed no cross-reactivity with antisera against protease from LG-12, *B. amyloliquefaciens, B. licheniformis* or *B. lentus*. LGX exhibited different kinetic properties than LG-12 and exhibited poor thermal stability.

As shown in FIG. 2, comparing the sequence of LG-12 protease and LGX protease with known sequences of *B.*

*amyloliquefaciens* and *B. alcalophilus* (*lentus*) proteases, demonstrates that LG-12 is 65% homologous with *B. amyloliquefaciens* and 64% homologous with *B. lentus*. In FIG. 1, the sequences of LG-12 and LGX are compared with subtilisins from *B. licheniformis*, *B. amyloliquefaciens*, and *B. lentus*. The sequences for *B. licheniformis* and *B. amyloliquefaciens* are from genes cloned at Genencor International, Inc. Sequences for *B. lentus* (Savinase™ and Esperase™) are from PCT patent application WO 89/06279, published Jul. 13, 1989, by Hastrup, et al.

Although the percent of homology between *B. lentus* and *B. amyloliquefaciens* is similar (64% versus 65% respectively) as compared to LG-12, a close comparison of the sequences would render one skilled in the art to classify LG-12 as more homologous to *B. amyloliquefaciens* than *B. lentus*. This is due to the lack of the deletion at residues 161–164 of the LG-12 enzyme as compared to the two *B. lentus* enzymes which have this deletion. Bacillus subtilisins having the deletion in this region (161–164) are typically classified as highly alkaline proteases. See Siezen, et al., Protein Engineering, Vol. 4, No. 7, 719–737, 1991. In addition, the *B. lentus* enzymes have deletions at positions 36 and 56 (as shown in FIG. 1) whereas LG-12 and *B. amyloliquefaciens* subtilisins do not.

Purification of LG-12 Protease

LG-12 protease was recovered by dialyzing cell broth against 10 mM TES buffer, at pH 6.2. The dialyzed broth was loaded on a DEAE-Trisacryl column. Unbound material was loaded on a CM-Trisacryl column. Absorbed enzyme was eluted with 10 mM TES, 0.4M NaCl at pH 6.2. This recovery and purification procedure was carried out substantially as described in Estell, et al., *supra*, incorporated herein.

LG-12 enzyme isolated and purified by methods described herein was used in the experiments detailed below. Cloned LG-12 expressed in *Bacillus subtilis* was used to measure thermal stability.

Formulations

The subtilisin enzymes useful in the present invention can be formulated as a purposefully added ingredient into any known powdered (granular) or liquid cleaning composition having a pH between about 6.5–12.0 at levels of about 0.01 to about 5% (preferably 0.05 to 0.5%) by weight of the cleaning composition. As used herein, a "cleaning effective amount" means between about 0.01 to about 5% enzyme by weight of the cleaning composition. These cleaning compositions can also include other enzymes such as other known proteases, amylases, lipases or cellulases (or components thereof), as well as bleaches, colorants, builders, stabilizers, emulsifiers, surfactants and any other known excipients.

The addition of LG-12 subtilisin to conventional cleaning compositions does not create any special use limitation. In other words, any temperature and pH suitable for such cleaning compositions containing enzymes is also suitable for the present compositions. Preferably, however, the present compositions may be used at higher temperatures and at higher pH.

When the enzymes of the present invention are encompassed in detergent formulations, they may be formulated with detergents or other surfactants in accord with methods known in the art for use in industrial processes, especially laundry. In laundry detergent compositions, the enzymes are combined with detergents, builders, bleach and/or fluorescent whitening agents. Suitable detergents include linear alkyl benzene sulfonates, alkyl ethoxylated sulfate, sulfated linear alcohol or ethoxylated linear alcohol. The compositions may be formulated in granular or liquid form.

Based on the profile of the preferred enzyme (LG-12), it is contemplated that this enzyme will be particularly useful in dishcare applications, which often require high temperatures and/or more alkaline pH. Such dishcare products can be liquid or granular for automatic dishwashers or for manual dishwashing.

One embodiment of the present invention comprises an automatic dishwashing detergent composition comprising a nonionic surface-active agent (surfactant) and a proteolytic enzyme. The surface-active component comprises at least about 0.5% of a nonionic surface-active agent. The surfactant level desirably is kept below about 20% in the case of a granular detergent composition. Using more than about 20% in the case of granular detergent can contribute to a lumping and caking tendency of the product. Examples of suitable automatic dishwashing detergents are described in U.S. Pat. No. 4,162,987, the disclosure of which is incorporated herein by reference. Other known dishwashing compositions are described in U.S. Pat. Nos. 4,753,748; 3,697,451; 4,501,681 and 4,591,448; which are incorporated herein by reference. The enzyme of the present invention may be used in any of these dishcare formulations.

The use of emulsifiers or surfactants (anionic, nonionic, or zwitterionic) may be used in the present compositions. Such emulsifiers and surfactants are described in U.S. Pat. No. 5,108,457, incorporated herein by reference.

Additional adjuncts of a wide variety may be considered for use in combination with the enzyme of the present invention, depending on the specific application contemplated. For example, the compositions of the present invention may include fragrances, dyes, builders (including alumino-silicate (Zeolite) builders), stabilizers, buffers, etc. Stabilizers may be included to achieve a number of purposes. For example, the stabilizers may be directed toward establishing and maintaining effectiveness of the enzymes from original formulation components or even intermediate products existing after the formulation is placed in an aqueous solution. Since enzymes may be hindered in hydrolysis of substrates because of heavy metals, organic compounds, etc., suitable stabilizers which are generally known in the art may be employed to counter such effects and achieve maximum effectiveness of the enzymes within the formulation.

Buffering agents maybe utilized to maintain desired pH levels for aqueous solutions. Buffering agents generally include all such materials which are well known to those skilled in the detergent art and include, but are not limited to, carbonates, phosphates, silicates, borates and hydroxides.

The following experimental methods and materials are described for purposes of illustrating the present invention. However, other aspects, advantages and modifications within the scope of the invention will be apparent to those skilled in the art to which the invention pertains.

EXPERIMENTAL

Example 1

Cloning of sprC Locus

Figure 4:
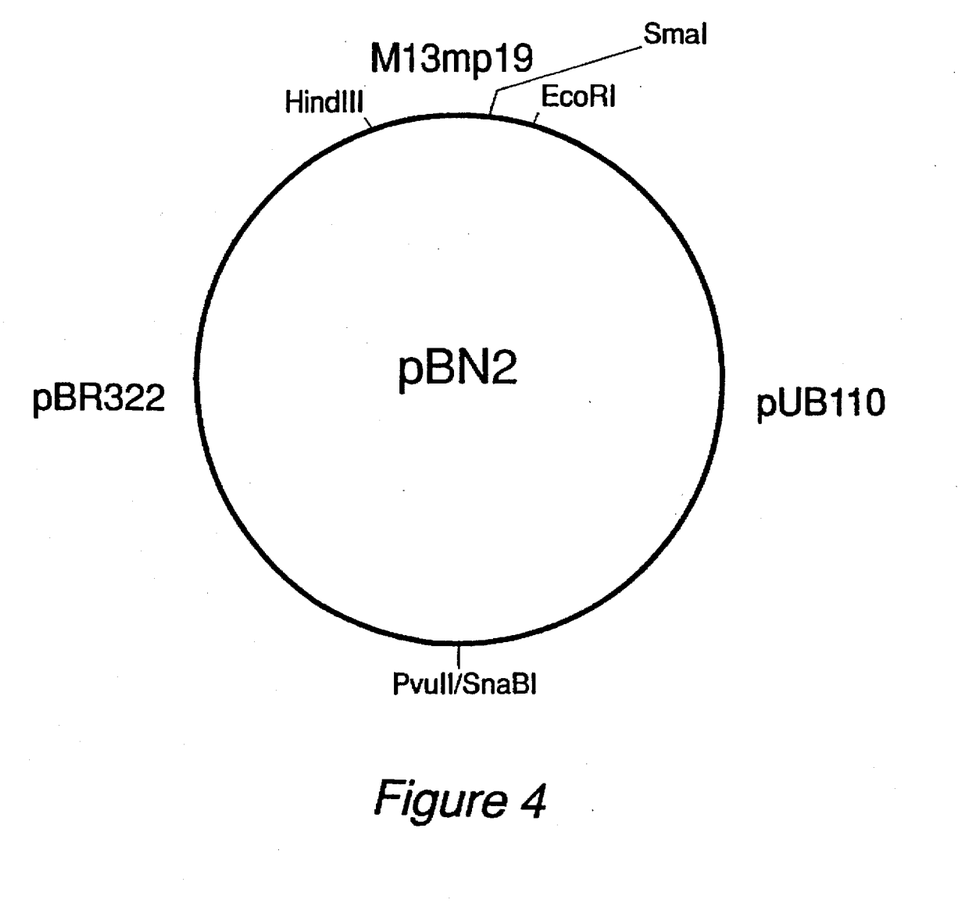
FIG. 4 shows a map of plasmid pBN2.

Nomenclature: In this example, the source for chromosomal DNA for cloning is *Bacillus sp.* LG-12. In the cloning experiments the host *E. coli* strains are MM294 and JM101 (see Sambrook, et al., Molecular Cloning, a Laboratory Manual (1989)) and the host Bacillus strain is BG2036, a variant of I168 which has been deleted for the two proteases, Npr and Apr, using methods described in Stahl, M. L., J. Bact. (1984) 158:411–418. All bacteria in this example are grown on Luria-Bertani medium or on 1.5% agar plates of the same composition, containing either ampicillin or neomycin where appropriate. DNA sequencing refers to the determination of the DNA nucleotide sequence through dideoxynucleotide termination sequencing (Ausubel, F. M.; Brent, R.; Kingston, R. E.; Moore, D. D.; Seidman, J. G.; Smith, J. A. and Struhl, K.; Short Protocols in Molecular Biology, (1989) 217–225). Bacillus shuttle vector pBN2 was derived by directly ligating the SnaBI/EcoRI fragment of pUB110, the HindIII/PvuII fragment of pBR322 and the HindIII/EcoRI polylinker fragment of M13mp19 (FIG. 4).

Figure 5A:
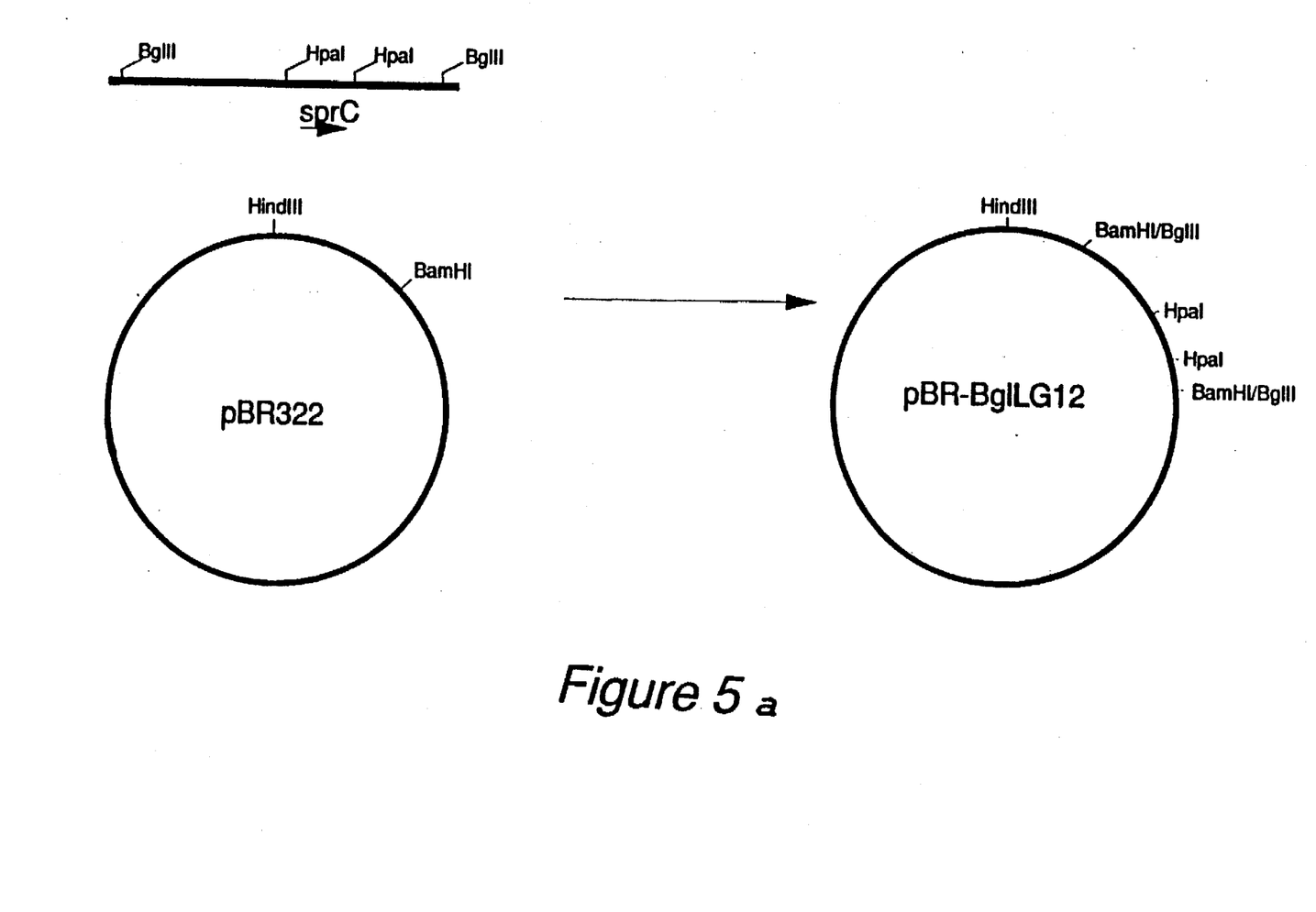
FIGS. 5a and b show a map for the cloning of sprC.
Figure 5B:
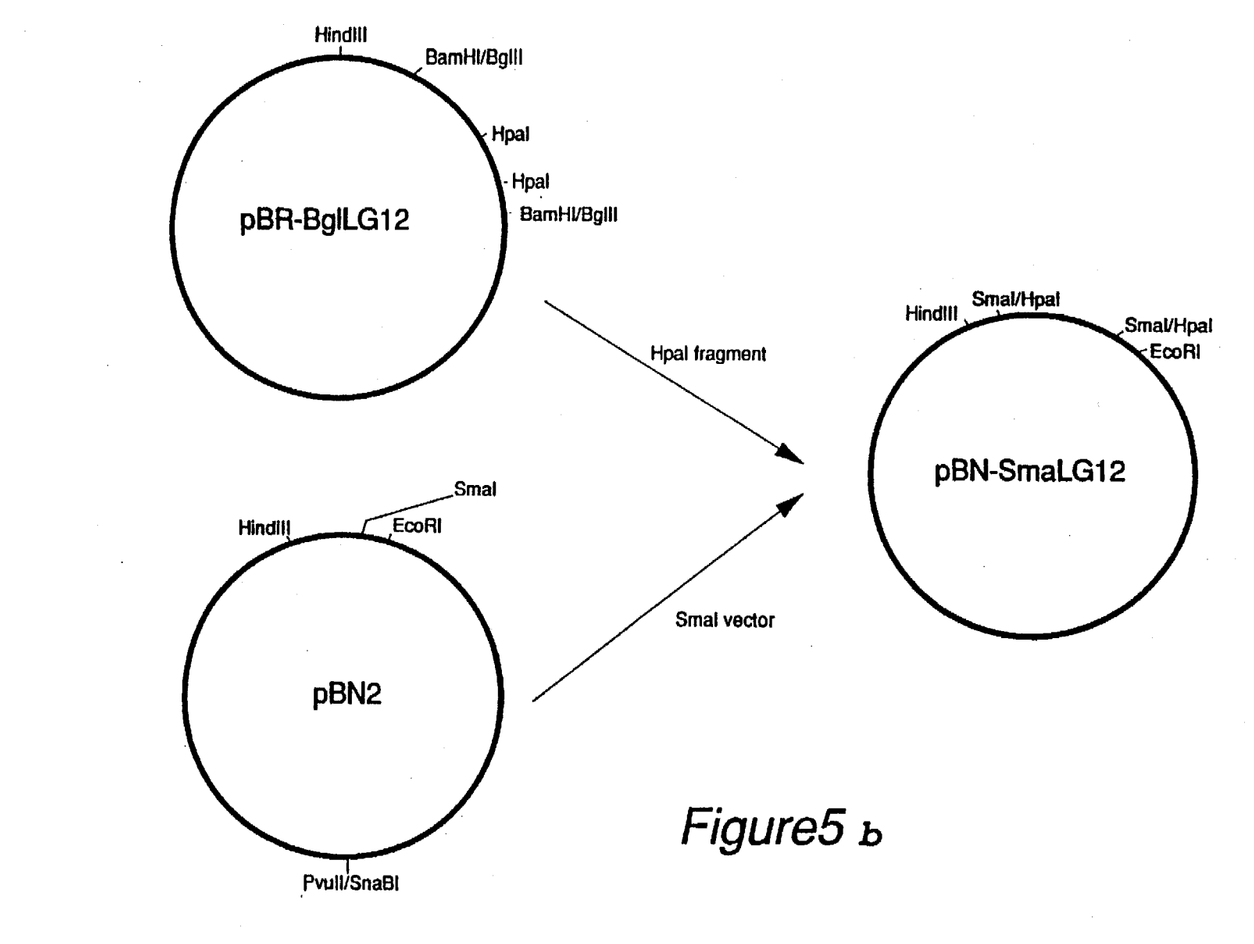

Cloning of sprC (FIGS. 5a and b): Chromosomal DNA was isolated from a 10 mL culture of Bacillus sp. LG-12 (Ausubel, F. M., et al., Short Protocols in Molecular Biology, (1989) p. 61). The purified DNA was digested with appropriate restriction enzymes (Perbal, B., A Practical Guide to Molecular Cloning, 2nd Ed. (1988) 327–339), fractionated on 0.8% agarose gels (Perbal, B., ibid., 340–349), and subjected to Southern analysis (Perbal, B., ibid., p. 443) on Nytran filters (S&S). The nick translated (Perbal, B., ibid., p. 439) probe used in the Souther analysis was a plasmid, pS4.5, containing the Bacillus amyloliquefaciens subtilisin aprE gene (Wells, J. A., et al., Nuc. Acids Res. 11:7911–7922 (1983). An 0.9 kb HindIII fragment, identified by this procedure was cloned into pBR322 which had been previously digested with HindIII and dephosphorylated with calf intestine alkaline phosphatase (Perbal, B., ibid., 403–404). The positive clones were identified by colony hybridization (Perbal, B., ibid., p. 439) and partially sequenced by subcloning into M13mp18 and M13mp19 (Perbal, B., ibid., 585–618). Sequencing of the fragment revealed an open reading frame with 50% identity to the C-terminal half of the probe amino acid sequence.

Figure 3:
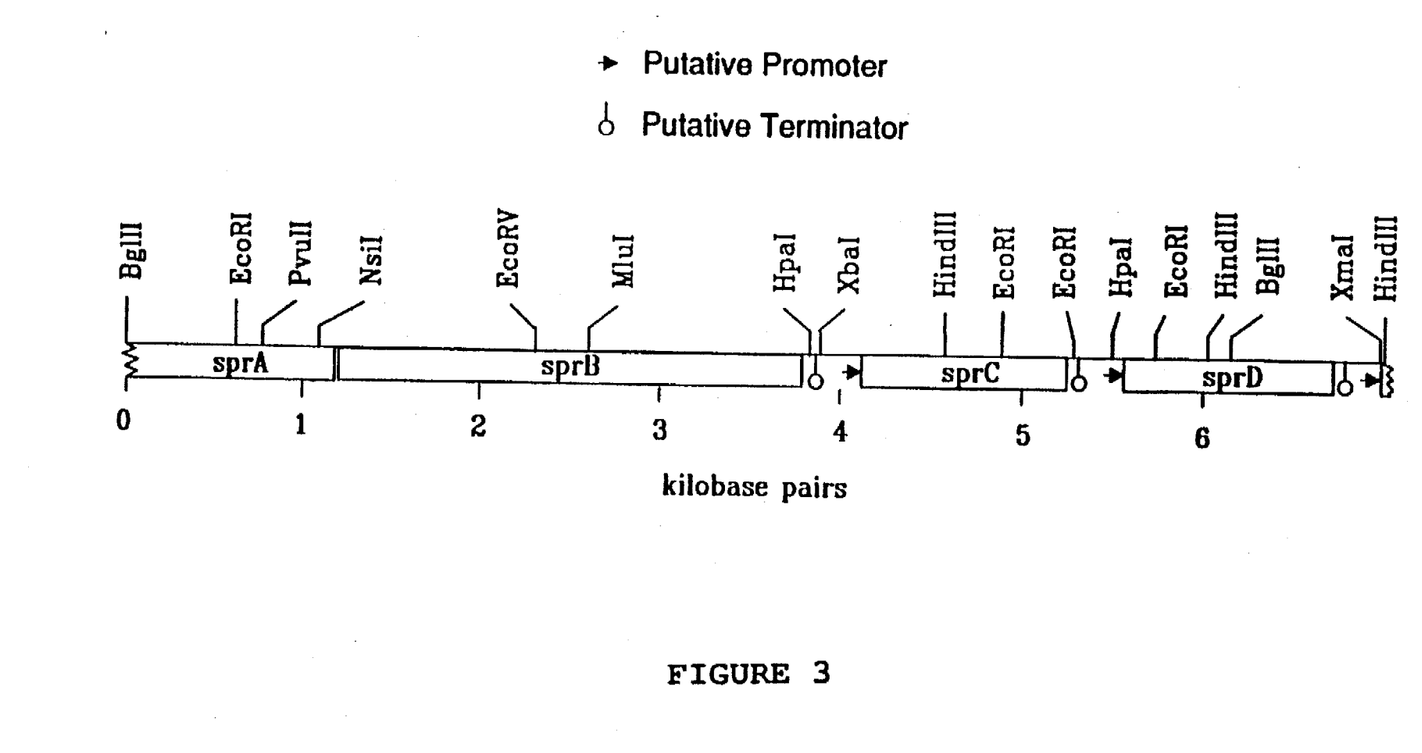
FIG. 3 shows a restriction map of the spr genes.

The upstream sequence together with several additional open reading frames (sprA, sprB, and sprC (see FIG. 3) ) was obtained by probing a BglII restricted Southern blot of the LG-12 chromosomal DNA with the nick translated 0.9 kb HindIII gene fragment. A 6.8 kb BglII fragment was cloned into the BamHI site of pBR322 and the appropriate transformant identified by colony hybridization (pBR-BglLG-12). This fragment was subcloned into M13mp18 and M13mp19 and the entire sequence determined in both directions. A representative restriction map of this area is shown in FIG. 3. The sprC gene was then subcloned on a HpaI fragment into the SmaI site of the Bacillus shuttle vector, pBN2, for expression in Bacillus subtilis (pBN-SmaLG-12). The final construction was transformed into Bacillus subtilis BG2036 (Anagnostopoulos, C., J. Bact. (1961) 81:741–746) and maintained as a replicating plasmid under neomycin selection.

Example 2

Native LG-12 subtilisin, isolated and purified by the methods described herein, was analyzed for its ability to hydrolyze various commercial synthetic substrates. Assays were done in 96 well microtiter plates at room temperature in 0.1M Tris-HCl, pH 8.6. For each substrate the final concentration in the reaction mixture is shown in Table I below. The data in Table I shows a comparison of the ability of LG-12 to hydrolyze such substrates versus proteases from known Bacillus organisms. Enzymes were diluted enough to give about 0.15 rate ($A_{410}$/min) in the regular cuvette assay. (Estell, et al., supra.)

TABLE I

| | Hydrolysis Rate ($A_{405}$/min) | | |
|---|---|---|---|
| Substrate (mg/ml)* | B. amylo | B. lentus | LG-12 |
| sAAPFpNA (0.8) | 0.83 | 1.15 | 0.87 |
| sAAPLpNA (0.8) | 0.45 | 0.23 | 0.58 |
| sAAPMpNA (0.8) | 0.25 | 0.75 | 0.19 |
| sAAApNA (2.0) | 0.011 | 0.176 | 0.014 |
| KAAFpNA (0.8) | 0.002 | 0.08 | 0.006 |
| VLKpNA (0.8) | 0.0017 | 0.0003 | 0.0008 |

*Substrate concentration is the final substrate concentration in the reaction mix.

As can be seen in Table I, all three enzymes showed significant hydrolysis of sAAA, sAAPM, sAAPF and sAAPL substrates. Other substrates were hydrolyzed at extremely slow rates. In order to achieve a better comparison of the enzymes, rates were expressed as a ratio with the sAAPFpNA rate. This comparison is shown in Table II below,

TABLE II

| | Ratio of sAAPFpNA/XXXpNA | | |
|---|---|---|---|
| Substrate | B. amylo | B. lentis | LG-12 |
| sAAPFpNA | 1 | 1 | 1 |
| sAAPLpNA | 1.8 | 6 | 1.5 |
| sAAPMpNA | 3.3 | 1.5 | 4.6 |
| sAAApNA | 75 | 6.5 | 62.1 |
| KAAFpNA | 461.1 | 14.4 | 145.0 |
| VLKpNA | 488.2 | 3833.3 | 1087.5 |

As can be seen from Table II, the substrate profile for LG-12 protease is more similar to B. amyloliquefaciens protease than the B. lentus (Savinase™) protease. For example, Savinase™ hydrolyzed sAAA at a proportionally higher rate (ratio of 6.5) than B. amyloliquefaciens protease and LG-12 protease (ratios of 75 and 62 respectively). On the other hand, LG-12 and B. amyloliquefaciens protease hydrolyzed sAAPLpNA (ratios 1.5 to 1.8) better than Savinase™ (ratio of 6).

Example 3

Using the cloned enzyme (as described in Example 1), pH stability of LG-12 was measured using the following protocol. The results are summarized in Table III below.

Method to Measure Protease pH Stability

Parameters: 15 ppm enzyme, 10 minutes at 60° C. without Ca++ and/or with 50 mM $CaCl_2$, measure stability at each pH unit from 4–11.

Buffer blend was prepared by mixing 50 mM each glycine, TAPS, PIPES and acetate. The pH of the buffer blend was adjusted at each unit between 4–11 so that the pH was corrected for the temperature effect as follows: a) 0.016 pH/° C. if buffer blend is pH 11–8; b) 0.011 pH/° C. if buffer blend is pH 7–6; and c) 0.006 pH/° C. if buffer blend is pH 5–4.

The protease sample was diluted to 30 ppm with the appropriate buffer blend from above. The sample was desalted using a Pharmacia PD-10 column, equilibrated with 25 mL of the appropriate buffer blend. To the column were added 2.5 mL of each 30 ppm sample and the samples were eluted with 3.5 mL buffer blend.

Samples were assayed using the sAAPFpNA assay (pH 8.6, 25° C.). The samples were adjusted to 15 ppm with buffer blend and $CaCl_2$ was added to achieve 50 mM $CaCl_2$ as needed. The sAAPFpNA activity was measured in duplicate at time 0, and then an aliquot of 200 uL was placed into 2 greased mini-Eppendorf centrifuge tubes. The tubes were placed in a Hybaid Thermal Reactor programmed to be at 60° C. for 10 minutes. After 10 minutes at the appropriate temperature the samples were immediately placed in an ice bath and cooled for 2 minutes and then assayed for remaining activity.

pH stability is expressed as the percentage of remaining activity=

$$\frac{\text{Activity at Time 10 (100)}}{\text{Activity at Time 0}} = \text{pH Stability \%}$$

TABLE III

| pH 60° C. | % Remaining Activity | | |
|---|---|---|---|
| | Savinase | BPN'* | LG-12 |
| A. pH Stability Without Ca++ | | | |
| 11 | 0 | 0 | 40 |
| 10 | 10.3 | 5 | 54 |
| 9 | 54 | 54 | 79 |
| 8 | 68 | 71 | 83 |
| 7 | 64 | 58 | 82 |
| 6 | 51 | 46 | 66 |
| 5 | 2.3 | 6 | 0 |
| 4 | 0 | 0 | 0 |
| B. pH Stability with Ca++ | | | |
| 11 | 74 | 60 | 93 |
| 10 | 92 | 96 | 100 |
| 9 | 92 | 100 | 100 |
| 8 | 100 | 100 | 94 |
| 7 | 99 | 100 | 96 |
| 6 | 100 | 100 | 93 |
| 5 | 100 | 91 | 90 |
| 4 | 45 | 40 | 24 |

*BPN' = B. amyloliquefaciens (Y217→L)

As can be seen from Table III, LG-12 enzyme without Ca++, at a pH>6, has an increased amount of enzymatic activity remaining and thus has a broader pH stability than Savinase™. For example, at pH 9, LG-12 has 79% activity reining whereas Savinase™ has only 54% activity remaining. As expected, all enzymes had enhanced pH stability in the presence of Ca++, but LG-12 had the best stability.

Example 4

Using the cloned enzyme (as described in Example 1), thermal stability of LG-12 was measured using the following protocol. The results are shown in Table IV.

Method to Measure Protease Thermal Stability

Parameters: 15 ppm enzyme, pH 10.0, 10 minutes at 60° C. without Ca++, 60° C. with 50 mM $CaCl_2$ or 70° C. with 50 mM $CaCl_2$.

Protease samples were diluted to 30 ppm with 100 mM glycine, pH 10.0 at 25° C. The samples were desalted using a Pharmacia PD-10 column, equilibrated with 25 mL 100 mM glycine, pH 10.0. To the column were added 2.5 mL of each 30 ppm sample, and each sample was eluted with 3.5 mL 100 mM glycine, pH 10.0.

Samples were assayed using the sAAPFpNA assay (pH 8.6, 25° C.). The samples were adjusted to 15 ppm with 100 mM glycine, pH 10.0, and $CaCl_2$ was added to achieve 50 mM $CaCl_2$ as needed. The sAAPFpNA activity of solutions with and without Ca++ was measured in duplicate at time 0 and an aliquot of 200 uL was added into greased mini-Eppendorf centrifuge tubes as follows: 1) 2 tubes for the 0 Ca++; b) 4 tubes for the 50 mM Ca++ (2 for 60° C. and 2 for 70° C.). The tubes were placed in a Hybaid Thermal Reactor programmed at 60° C. or 70° C. for 10 minutes. After 10 minutes at the appropriate temperature the tubes were immediately placed in an ice bath and cooled for 2 minutes, and then assayed for remaining activity.

Thermal stability is expressed as the percentage of remaining activity=

$$\frac{\text{Activity at Time 10 (100)}}{\text{Activity at Time 0}} = \text{Thermal Stability \%}$$

TABLE IV

| Enzyme | % Remaining Activity | | |
|---|---|---|---|
| | 60° C. 0 Ca++ | 60° C. w/Ca++ | 70° C. w/Ca++ |
| Maxatase (licheniformis) | 21 | 83 | 2.4 |
| Esperase (lentus) | 89 | 98 | 88 |
| Savinase (lentus) | 8.6 | 95 | 69 |
| LG-12 | 60 | 97 | 82 |

As can be seen from Table IV, LG-12 enzyme and Esperase™ exhibited enhanced stability in the presence or absence of calcium ions.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 275 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

| Ala | Gln | Thr | Val | Pro | Trp | Gly | Ile | Pro | His | Ile | Lys | Ala | Asp | Lys | Ala |
|---|---|---|---|---|---|---|---|---|---|---|---|---|---|---|---|
| 1 | | | | 5 | | | | | 10 | | | | | 15 | |

|     |     |     |     |     |     |     |     |     |     |     |     |     |     |     |
|-----|-----|-----|-----|-----|-----|-----|-----|-----|-----|-----|-----|-----|-----|-----|
| His | Ala | Ala | Gly | Val | Thr | Gly | Ser | Gly | Val | Lys | Val | Ala | Ile | Leu | Asp |
|     |     |     | 20  |     |     |     | 25  |     |     |     |     | 30  |     |     |
| Thr | Gly | Ile | Asp | Ala | Asn | His | Ala | Asp | Leu | Asn | Val | Lys | Gly | Gly | Ala |
|     |     | 35  |     |     |     | 40  |     |     |     |     | 45  |     |     |     |
| Ser | Phe | Val | Ser | Gly | Glu | Pro | Asn | Ala | Leu | Gln | Asp | Gly | Asn | Gly | His |
|     | 50  |     |     |     | 55  |     |     |     |     | 60  |     |     |     |     |
| Gly | Thr | His | Val | Ala | Gly | Thr | Val | Ala | Ala | Leu | Asn | Asn | Thr | Thr | Gly |
| 65  |     |     |     | 70  |     |     |     |     | 75  |     |     |     |     | 80  |
| Val | Leu | Gly | Val | Ala | Tyr | Asn | Ala | Asp | Leu | Tyr | Ala | Val | Lys | Val | Leu |
|     |     |     |     | 85  |     |     |     | 90  |     |     |     |     | 95  |     |
| Ser | Ala | Ser | Gly | Ser | Gly | Thr | Leu | Ser | Gly | Ile | Ala | Gln | Gly | Ile | Glu |
|     |     |     | 100 |     |     |     | 105 |     |     |     |     | 110 |     |     |
| Trp | Ser | Ile | Ser | Asn | Gly | Met | Asn | Val | Ile | Asn | Met | Ser | Leu | Gly | Gly |
|     |     | 115 |     |     |     | 120 |     |     |     |     | 125 |     |     |     |
| Ser | Ser | Gly | Ser | Thr | Ala | Leu | Gln | Gln | Ala | Cys | Asn | Asn | Ala | Tyr | Asn |
|     | 130 |     |     |     | 135 |     |     |     |     | 140 |     |     |     |     |
| Arg | Gly | Ile | Val | Val | Ile | Ala | Ala | Ala | Gly | Asn | Ser | Gly | Ser | Ser | Gly |
| 145 |     |     |     | 150 |     |     |     |     | 155 |     |     |     |     | 160 |
| Asn | Arg | Asn | Thr | Met | Gly | Tyr | Pro | Ala | Arg | Tyr | Ser | Ser | Val | Ile | Ala |
|     |     |     | 165 |     |     |     | 170 |     |     |     |     | 175 |     |     |
| Val | Gly | Ala | Val | Ser | Ser | Asn | Asn | Thr | Arg | Ala | Ser | Phe | Ser | Ser | Val |
|     |     |     | 180 |     |     |     | 185 |     |     |     |     | 190 |     |     |
| Gly | Ser | Glu | Leu | Glu | Val | Met | Ala | Pro | Gly | Val | Asn | Ile | Leu | Ser | Thr |
|     | 195 |     |     |     | 200 |     |     |     |     | 205 |     |     |     |     |
| Thr | Pro | Gly | Asn | Asn | Tyr | Ala | Ser | Phe | Asn | Gly | Thr | Ser | Met | Ala | Ala |
| 210 |     |     |     |     | 215 |     |     |     |     | 220 |     |     |     |     |
| Pro | His | Val | Ala | Gly | Ala | Ala | Ala | Leu | Ile | Lys | Ala | Lys | Tyr | Pro | Ser |
| 225 |     |     |     | 230 |     |     |     |     | 235 |     |     |     |     | 240 |
| Met | Thr | Asn | Val | Gln | Ile | Arg | Glu | Arg | Leu | Lys | Asn | Thr | Ala | Thr | Asn |
|     |     |     | 245 |     |     |     | 250 |     |     |     |     | 255 |     |     |
| Leu | Gly | Asp | Pro | Phe | Phe | Tyr | Gly | Lys | Gly | Val | Ile | Asn | Val | Glu | Ser |
|     |     |     | 260 |     |     |     | 265 |     |     |     |     | 270 |     |     |
| Ala | Leu | Gln |     |     |     |     |     |     |     |     |     |     |     |     |
|     |     | 275 |     |     |     |     |     |     |     |     |     |     |     |     |

( 2 ) INFORMATION FOR SEQ ID NO:2:

( i ) SEQUENCE CHARACTERISTICS:
        ( A ) LENGTH: 274 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

|     |     |     |     |     |     |     |     |     |     |     |     |     |     |     |     |
|-----|-----|-----|-----|-----|-----|-----|-----|-----|-----|-----|-----|-----|-----|-----|-----|
| Ala | Gln | Thr | Val | Pro | Tyr | Gly | Ile | Pro | Leu | Ile | Lys | Ala | Asp | Lys | Val |
| 1   |     |     |     | 5   |     |     |     |     | 10  |     |     |     |     | 15  |     |
| Gln | Ala | Gln | Gly | Phe | Lys | Gly | Ala | Asn | Val | Lys | Val | Ala | Val | Leu | Asp |
|     |     |     | 20  |     |     |     | 25  |     |     |     |     | 30  |     |     |     |
| Thr | Gly | Ile | Gln | Ala | Ser | His | Pro | Asp | Leu | Asn | Val | Val | Gly | Gly | Ala |
|     |     | 35  |     |     |     | 40  |     |     |     |     | 45  |     |     |     |
| Ser | Phe | Val | Ala | Gly | Glu | Ala | Tyr | Asn | Thr | Asp | Gly | Asn | Gly | His | Gly |
|     | 50  |     |     |     | 55  |     |     |     |     | 60  |     |     |     |     |
| Thr | His | Val | Ala | Gly | Thr | Val | Ala | Ala | Leu | Asp | Asn | Thr | Thr | Gly | Val |
| 65  |     |     |     | 70  |     |     |     |     | 75  |     |     |     |     | 80  |

|     |     |     |     |     |     |     |     |     |     |     |     |     |     |     |     |
|---|---|---|---|---|---|---|---|---|---|---|---|---|---|---|---|
| Leu | Gly | Val | Ala | Pro<br>85 | Ser | Val | Ser | Leu | Tyr<br>90 | Ala | Val | Lys | Val | Leu<br>95 | Asn |
| Ser | Ser | Gly | Ser<br>100 | Gly | Thr | Tyr | Ser | Gly<br>105 | Ile | Val | Ser | Gly<br>110 | Ile | Glu | Trp |
| Ala | Thr | Thr<br>115 | Asn | Gly | Met | Asp<br>120 | Val | Ile | Asn | Met | Ser<br>125 | Leu | Gly | Gly | Pro |
| Ser | Gly<br>130 | Ser | Thr | Ala | Met | Lys<br>135 | Gln | Ala | Val | Asp | Asn<br>140 | Ala | Tyr | Ala | Arg |
| Gly<br>145 | Val | Val | Val | Val<br>150 | Ala | Ala | Ala | Gly | Asn<br>155 | Ser | Gly | Ser | Ser | Gly | Asn<br>160 |
| Thr | Asn | Thr | Ile | Gly<br>165 | Tyr | Pro | Ala | Lys | Tyr<br>170 | Asp | Ser | Val | Ile | Ala<br>175 | Val |
| Gly | Ala | Val | Asp<br>180 | Ser | Asn | Ser | Asn | Arg<br>185 | Ala | Ser | Phe | Ser | Ser<br>190 | Val | Gly |
| Ala | Glu | Leu<br>195 | Glu | Val | Met | Ala | Pro<br>200 | Gly | Ala | Gly | Val | Tyr<br>205 | Ser | Thr | Tyr |
| Pro | Thr<br>210 | Ser | Thr | Tyr | Ala | Thr<br>215 | Leu | Asn | Gly | Thr | Ser<br>220 | Met | Ala | Ser | Pro |
| His<br>225 | Val | Ala | Gly | Ala | Ala<br>230 | Ala | Leu | Ile | Leu | Ser<br>235 | Lys | His | Pro | Asn | Leu<br>240 |
| Ser | Ala | Ser | Gln | Val<br>245 | Arg | Asn | Arg | Leu | Ser<br>250 | Ser | Thr | Ala | Thr | Tyr<br>255 | Leu |
| Gly | Ser | Ser | Phe<br>260 | Tyr | Tyr | Gly | Lys | Gly<br>265 | Leu | Ile | Asn | Val | Glu<br>270 | Ala | Ala |
| Ala | Gln |     |     |     |     |     |     |     |     |     |     |     |     |     |     |

(2) INFORMATION FOR SEQ ID NO:3:

(i) SEQUENCE CHARACTERISTICS:
        (A) LENGTH: 275 amino acids
        (B) TYPE: amino acid
        (C) STRANDEDNESS: single
        (D) TOPOLOGY: linear     (ii) MOLECULE TYPE: protein     (xi) SEQUENCE DESCRIPTION: SEQ ID NO:3:

|     |     |     |     |     |     |     |     |     |     |     |     |     |     |     |     |
|---|---|---|---|---|---|---|---|---|---|---|---|---|---|---|---|
| Ala<br>1 | Gln | Ser | Val | Pro<br>5 | Tyr | Gly | Val | Ser | Gln<br>10 | Ile | Lys | Ala | Pro | Ala<br>15 | Leu |
| His | Ser | Gln | Gly<br>20 | Tyr | Thr | Gly | Ser | Asn<br>25 | Val | Lys | Val | Ala | Val<br>30 | Ile | Asp |
| Ser | Gly | Ile<br>35 | Asp | Ser | Ser | His | Pro<br>40 | Asp | Leu | Lys | Val | Ala<br>45 | Gly | Gly | Ala |
| Ser | Met<br>50 | Val | Pro | Ser | Glu | Thr<br>55 | Asn | Pro | Phe | Gln | Asp<br>60 | Asn | Asn | Ser | His |
| Gly<br>65 | Thr | His | Val | Ala | Gly<br>70 | Thr | Val | Ala | Ala | Leu<br>75 | Asn | Asn | Ser | Ile | Gly<br>80 |
| Val | Leu | Gly | Val | Ala<br>85 | Pro | Ser | Ala | Ser | Leu<br>90 | Tyr | Ala | Val | Lys | Val<br>95 | Leu |
| Gly | Ala | Asp | Gly<br>100 | Ser | Gly | Gln | Tyr | Ser<br>105 | Trp | Ile | Ile | Asn | Gly<br>110 | Ile | Glu |
| Trp | Ala | Ile<br>115 | Ala | Asn | Asn | Met | Asp<br>120 | Val | Ile | Asn | Met | Ser<br>125 | Leu | Gly | Gly |
| Pro | Ser<br>130 | Gly | Ser | Ala | Ala | Leu<br>135 | Lys | Ala | Ala | Val | Asp<br>140 | Lys | Ala | Val | Ala |
| Ser<br>145 | Gly | Val | Val | Val | Val<br>150 | Ala | Ala | Ala | Gly | Asn<br>155 | Glu | Gly | Thr | Ser | Gly<br>160 |

```
Ser  Ser  Ser  Thr  Val  Gly  Tyr  Pro  Gly  Lys  Tyr  Pro  Ser  Val  Ile  Ala
               165                      170                      175

Val  Gly  Ala  Val  Asp  Ser  Ser  Asn  Gln  Arg  Ala  Ser  Phe  Ser  Ser  Val
               180                      185                      190

Gly  Pro  Glu  Leu  Asp  Val  Met  Ala  Pro  Gly  Val  Ser  Ile  Gln  Ser  Thr
          195                      200                      205

Leu  Pro  Gly  Asn  Lys  Tyr  Gly  Ala  Tyr  Asn  Gly  Thr  Ser  Met  Ala  Ser
          210                      215                      220

Pro  His  Val  Ala  Gly  Ala  Ala  Leu  Ile  Leu  Ser  Lys  His  Pro  Asn
225                      230                      235                      240

Trp  Thr  Asn  Thr  Gln  Val  Arg  Ser  Ser  Leu  Glu  Asn  Thr  Thr  Thr  Lys
                    245                      250                      255

Leu  Gly  Asp  Ser  Phe  Tyr  Tyr  Gly  Lys  Gly  Leu  Ile  Asn  Val  Gln  Ala
               260                      265                      270

Ala  Ala  Gln
          275
```

( 2 ) INFORMATION FOR SEQ ID NO:4:

( i ) SEQUENCE CHARACTERISTICS:
        ( A ) LENGTH: 268 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:4:

```
Gln  Thr  Val  Val  Trp  Gly  Ile  Ser  Phe  Ile  Asn  Thr  Gln  Gln  Ala  His
1                   5                        10                      15

Asn  Arg  Gly  Ile  Phe  Gly  Asn  Gly  Ala  Arg  Val  Ala  Val  Leu  Asp  Thr
               20                       25                      30

Gly  Ile  Ala  Thr  His  Pro  Asp  Leu  Arg  Ile  Ala  Gly  Gly  Ala  Ser  Phe
               35                       40                      45

Ile  Ser  Ser  Glu  Pro  Ser  Tyr  His  Asp  Asn  Asn  Gly  His  Gly  Thr  His
     50                       55                      60

Val  Ala  Gly  Thr  Ile  Ala  Ala  Leu  Asn  Asn  Ser  Ile  Gly  Val  Leu  Gly
65                       70                      75                      80

Val  Ala  Pro  Ser  Ala  Asp  Leu  Tyr  Ala  Val  Lys  Val  Leu  Asp  Arg  Asn
               85                       90                      95

Gly  Ser  Gly  Ser  Leu  Ala  Ser  Val  Ala  Gln  Gly  Ile  Glu  Trp  Ala  Ile
               100                      105                     110

Asn  Asn  Asn  Met  His  Ile  Ile  Asn  Met  Ser  Leu  Gly  Ser  Thr  Ser  Gly
          115                      120                      125

Ser  Ser  Thr  Leu  Glu  Leu  Ala  Val  Asn  Arg  Ala  Asn  Asn  Ala  Gly  Ile
          130                      135                      140

Leu  Leu  Val  Gly  Ala  Ala  Gly  Asn  Thr  Gly  Arg  Gln  Gly  Val  Asn  Tyr
145                      150                      155                     160

Pro  Ala  Arg  Tyr  Ser  Gly  Val  Met  Ala  Val  Ala  Ala  Val  Asp  Gln  Asn
               165                      170                      175

Gly  Gln  Pro  Pro  Ser  Phe  Ser  Thr  Tyr  Gly  Pro  Glu  Ile  Glu  Ile  Ser
               180                      185                      190

Ala  Pro  Gly  Val  Asn  Val  Asn  Ser  Thr  Tyr  Thr  Gly  Asn  Arg  Tyr  Val
          195                      200                      205

Ser  Leu  Ser  Gly  Thr  Ser  Met  Ala  Thr  Pro  His  Val  Ala  Gly  Val  Ala
          210                      215                      220
```

```
Ala  Leu  Val  Lys  Ser  Arg  Tyr  Pro  Ser  Tyr  Thr  Asn  Asn  Gln  Ile  Arg
225                 230                      235                           240

Gln  Arg  Ile  Asn  Gln  Thr  Ala  Thr  Tyr  Leu  Gly  Ser  Pro  Ser  Leu  Tyr
                    245                      250                      255

Gly  Asn  Gly  Leu  Val  His  Ala  Gly  Arg  Ala  Thr  Gln
               260                      265
```

( 2 ) INFORMATION FOR SEQ ID NO:5:

( i ) SEQUENCE CHARACTERISTICS:
  ( A ) LENGTH: 269 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:5:

```
Ala  Gln  Ser  Val  Pro  Trp  Gly  Ile  Ser  Arg  Val  Gln  Ala  Pro  Ala  Ala
1                     5                      10                           15

His  Asn  Arg  Gly  Leu  Thr  Gly  Ser  Gly  Val  Lys  Val  Ala  Val  Leu  Asp
               20                      25                      30

Thr  Gly  Ile  Ser  Thr  His  Pro  Asp  Leu  Asn  Ile  Arg  Gly  Gly  Ala  Ser
               35                      40                      45

Phe  Val  Pro  Gly  Glu  Pro  Ser  Thr  Gln  Asp  Gly  Asn  Gly  His  Gly  Thr
     50                      55                           60

His  Val  Ala  Gly  Thr  Ile  Ala  Ala  Leu  Asn  Asn  Ser  Ile  Gly  Val  Leu
65                       70                      75                           80

Gly  Val  Ala  Pro  Ser  Ala  Glu  Leu  Tyr  Ala  Val  Lys  Val  Leu  Gly  Ala
                    85                      90                           95

Ser  Gly  Ser  Gly  Ser  Val  Ser  Ser  Ile  Ala  Gln  Gly  Leu  Glu  Trp  Ala
               100                     105                     110

Gly  Asn  Asn  Gly  Met  His  Val  Ala  Asn  Leu  Ser  Leu  Gly  Ser  Pro  Ser
          115                     120                     125

Pro  Ser  Ala  Thr  Leu  Glu  Gln  Ala  Val  Asn  Ser  Ala  Thr  Ser  Arg  Gly
     130                     135                     140

Val  Leu  Val  Val  Ala  Ala  Ser  Gly  Asn  Ser  Gly  Ala  Gly  Ser  Ile  Ser
145                     150                     155                          160

Tyr  Pro  Ala  Arg  Tyr  Ala  Asn  Ala  Met  Ala  Val  Gly  Ala  Thr  Asp  Gln
               165                     170                     175

Asn  Asn  Asn  Arg  Ala  Ser  Phe  Ser  Gln  Tyr  Gly  Ala  Gly  Leu  Asp  Ile
               180                     185                     190

Val  Ala  Pro  Gly  Val  Asn  Val  Gln  Ser  Thr  Tyr  Pro  Gly  Ser  Thr  Tyr
          195                     200                     205

Ala  Ser  Leu  Asn  Gly  Thr  Ser  Met  Ala  Thr  Pro  His  Val  Ala  Gly  Ala
     210                     215                     220

Ala  Ala  Leu  Val  Lys  Gln  Lys  Asn  Pro  Ser  Trp  Ser  Asn  Val  Gln  Ile
225                     230                     235                          240

Arg  Asn  His  Leu  Lys  Asn  Thr  Ala  Thr  Ser  Leu  Gly  Ser  Thr  Asn  Leu
               245                     250                     255

Tyr  Gly  Ser  Gly  Leu  Val  Asn  Ala  Glu  Ala  Ala  Thr  Arg
               260                     265
```

( 2 ) INFORMATION FOR SEQ ID NO:6:

( i ) SEQUENCE CHARACTERISTICS:
  ( A ) LENGTH: 269 amino acids
  ( B ) TYPE: amino acid
  ( C ) STRANDEDNESS: single (D) TOPOLOGY: linear (ii) MOLECULE TYPE: protein (xi) SEQUENCE DESCRIPTION: SEQ ID NO:6:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:7:

(i) SEQUENCE CHARACTERISTICS:
(A) LENGTH: 276 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:7:

```
Ala Gln Thr Val Pro Tyr Gly Val Pro His Ile Lys Ala Asp Val Ala
 1               5                  10                  15

His Ala Gln Asn Val Thr Gly Ser Gly Val Lys Val Ala Val Leu Asp
            20                  25                  30

Thr Gly Ile Asp Ala Ser His Glu Asp Leu Arg Val Val Gly Gly Ala
        35                  40                  45

Ser Phe Val Ser Glu Glu Pro Asp Ala Leu Thr Asp Gly Asn Gly His
```

-continued

|   |   |   |   | 50 |   |   |   |   | 55 |   |   |   |   | 60 |   |
|---|---|---|---|---|---|---|---|---|---|---|---|---|---|---|---|
| Gly 65 | Thr | His | Val | Ala | Gly 70 | Thr | Ile | Ala | Ala | Leu 75 | Asn | Asn | Asn | Val | Gly 80 |
| Val | Leu | Gly | Val | Ser 85 | Tyr | Asp | Val | Asp | Leu 90 | Tyr | Ala | Val | Lys | Val 95 | Leu |
| Ser | Ala | Gly | Gly 100 | Ser | Gly | Thr | Leu | Ala 105 | Gly | Ile | Ala | Gln | Gly 110 | Ile | Glu |
| Trp | Ala | Ile 115 | Asp | Asn | Asn | Met | Asp 120 | Val | Ile | Asn | Met | Ser 125 | Leu | Gly | Gly |
| Ser | Thr 130 | Gly | Ser | Thr | Thr | Leu 135 | Lys | Gln | Ala | Ser | Asp 140 | Asn | Ala | Tyr | Asn |
| Ser 145 | Gly | Ile | Val | Val | Ile 150 | Ala | Ala | Ala | Gly | Asn 155 | Ser | Gly | Ser | Val | Leu 160 |
| Gly | Leu | Val | Asn | Thr 165 | Ile | Gly | Tyr | Pro | Ala 170 | Arg | Tyr | Asp | Ser | Val 175 | Ile |
| Ala | Val | Gly | Ala 180 | Val | Asp | Ser | Asn | Asn 185 | Asn | Arg | Ala | Ser | Phe 190 | Ser | Ser |
| Val | Gly | Ser 195 | Gln | Leu | Glu | Val | Met 200 | Ala | Pro | Gly | Val | Ala 205 | Ile | Asn | Ser |
| Thr | Leu 210 | Pro | Gly | Asn | Gln | Tyr 215 | Gly | Glu | Leu | Asn | Gly 220 | Thr | Ser | Met | Ala |
| Ser 225 | Pro | His | Val | Ala | Gly 230 | Ala | Ala | Ala | Leu | Leu 235 | Leu | Ala | Gln | Asn | Pro 240 |
| Asn | Leu | Thr | Asn | Val 245 | Gln | Val | Arg | Glu | Arg 250 | Leu | Arg | Asp | Thr | Ala 255 | Thr |
| Asn | Leu | Gly | Ser 260 | Ala | Phe | Asn | Tyr | Gly 265 | His | Gly | Val | Ile | Asn 270 | Leu | Glu |
| Arg | Ala | Leu 275 | Gln |   |   |   |   |   |   |   |   |   |   |   |   |

What is claimed is:

1. An improved cleaning composition comprising a cleaning effective amount of an isolated proteolytic enzyme the improvement comprising using a proteolytic enzyme characterized by the amino acid sequence of Seq. ID No. 1, having a pH stability profile of from about pH 6–11, such that 40% or more of the enzyme activity remains at a pH from about 6–11, and a suitable cleaning formulation.

2. A composition of claim 1 wherein the proteolytic enzyme is a subtilisin derived from a *Bacillus sp.* strain LG-12.

3. A composition of claim 1 wherein the enzyme is made by a process comprising transforming a host cell with a gene coding for the amino acid sequence of Seq. ID No. 1 and expressing the transformant.

4. A composition of claim 3 wherein the gene is sprC.

5. A composition of claim 3 wherein the host cell is a Bacillus strain.

6. A composition of claim 5 wherein the host cell is Bacillus subtilis.

7. A composition of claim 1 wherein the formulation is a detergent selected from the group consisting of a linear alkyl benzene sulfonate, alkyl benzene sulfate, sulfated linear alcohol, or ethoxylated linear alcohol.

8. A composition of claim 1 wherein the formulation is liquid or granular.

9. A composition of claim 1 further comprising one or more surfactants.

10. A composition of claim 1 wherein the formulation is a dishcare detergent composition.

11. A cleaning composition of claim 1 further comprising one or more additional enzyme selected from the group consisting of protease, amylase, lipase and cellulase or components of cellulase.

* * * * *